(12) United States Patent
Griesbach et al.

(10) Patent No.: US 6,497,865 B1
(45) Date of Patent: *Dec. 24, 2002

(54) COSMETIC HAIR CARE PREPARATIONS

(75) Inventors: Ute Griesbach, Dusseldorf (DE); Bernd Fabry, Korschenbroich (DE); Rolf Wachter, Dusseldorf (DE); Rolf E. Engstad, Tromso (NO)

(73) Assignee: Biotec Pharmacon ASA, Tromso (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/936,788

(22) PCT Filed: Mar. 3, 2000

(86) PCT No.: PCT/EP00/01834

§ 371 (c)(1),
(2), (4) Date: Jan. 23, 2002

(87) PCT Pub. No.: WO00/54737

PCT Pub. Date: Sep. 21, 2000

(30) Foreign Application Priority Data

Mar. 12, 1999 (DE) .......................... 199 11 057

(51) Int. Cl.$^7$ .......................... A61K 7/06; A61K 7/00; A61K 35/78; A61K 31/715

(52) U.S. Cl. .................. 424/70.1; 424/59; 424/400; 424/401; 424/195.16; 514/54

(58) Field of Search .................. 424/70.1, 400, 424/401, 195.16, 59; 514/54

(56) References Cited

U.S. PATENT DOCUMENTS 3,507,290 A    4/1970    Halleck

FOREIGN PATENT DOCUMENTS

| EP | 0074819 | 3/1983 |
| GB | 2286530 | 8/1995 |
| WO | WO9702007 | 1/1997 |

*Primary Examiner*—Shelley A. Dodson
(74) *Attorney, Agent, or Firm*—Ladas & Parry

(57) ABSTRACT

The invention relates to cosmetic hair care preparations containing: (a) water soluble β-(1,3) glucans which are substantially devoid of β-(1,6) links, and (b) polymers. The addition of the special glucans to the polymers reduces the formation of stress-cracking in the polymer films when the preparation is absorbed by the hair.

10 Claims, No Drawings

COSMETIC HAIR CARE PREPARATIONS

THE FIELD OF THE INVENTION

The invention belongs to the field of the hair cosmetics and concerns preparations with preferably film forming polymers and specific glucans as well as the use of these mixtures for the production of agents for hair treatment.

PRIOR ART

Hair cosmetic preparations, such as for example hair finishes or styling agents, contain as consolidation agents polymers, preferably of the type of polyvinyl pyrrolidone/vinyl acetate, which are taken up on the keratin fibres and give them the desired firmness. However, a disadvantage is the fact that the films after being applied a number of times after the drying easily become brittle and then not only the styling effect disappears, but the hair can also be damaged. Accordingly, it has been suggested in the German Offenlegungsschrift DE-A1 19524125 (Henkel) to add to the polymers small amounts of chitosan. These relief measures are in many cases not adequate.

The task of the invention has consisted in making cosmetic agents available, which as film forming agents contain polymers, especially polyvinyl pyrrolidone/vinyl acetate copolymers, and which tendency to the forming of stress cracks by at least equal hardness of the films is significantly decreased.

DESCRIPTION OF THE INVENTION

The object of the invention is hair care preparations, containing
(a) water soluble β-(1,3) glucans, substantially free from β-(1,6)-linkages, and
(b) polymers.

Surprisingly, it was found, that the addition of only very small amounts of the specific glucans to polymers, especially known film forming polymers, such as e.g. polyvinyl pyrrolidone/vinyl acetate copolymers, have effect on the control of the moisture and that the tendency to forming of stress crack decreases in a synergistic manner, whilst the hardness of the films are not adversely influenced, but often in addition improved. In this connection it should especially be emphasized that glucans with poor water solubility and/or with contents of 1,6-linkages in mixture with the polymers virtually have no influence on the formation of the stress cracks.

Water Soluble II-(1,3) Glucans

The term glucans is intended to mean homopolysaccharides based on glucose. Depending on sterical linking there is a difference between β-(1,3), β-(1,4) and β-(1,6) glucans. β-(1,3) Glucans normally show a helical structure, whereas glucans with a (1,4) linkage generally have a linear structure. The β-glucans of the invention have a (1,3) structure, i.e. they are substantillay free from undesired (1,6) linkages. Preferably such β-(1,3) glucans are used where the side chains exclusively show (1,3) linkages. Especially the agents contain glucans which are obtained on the basis of yeast from the family Sacchaomyces, especially *Saccharomyces cerevisiae*. Glucans of this type are available in technical amounts according to known methods. The international patent application WO 95/30022 (Biotec-Mackzymal) describes e.g. a method for producing such substances, wherein glucans with β-(1,3) and β-(1,6) linkages are brought in contact with β-(1,6) glucanases in such a way, that practically all β-(1,6) linkages are loosened. Preferably used for the manufacture of these glucans are glucanases based on *Trichodermia harzianum*. As to the manufacture and availability of the glucans contained in these agents, reference is made to the above cited publication.

Polymers

As anionic, non-ionic, amphoteric or zwitterionic polymers can for example the following be used: Polyacrylates, such as e.g. Advantage® CP, Copolymer VC 713, H2OLD EP-1 (ISP), Amphomer®, Versatyl® 90 (National Starch), Luviflex® VBM 35, Luvimer®, Ultrahold® 8, Ultrahold® Strong (BASF), vinyl acetate/crotonic acid copolymers, vinyl pyrrolidone/vinyl acrylate copolymers, vinyl acetate/butyl maleate/isoboryl acrylate copolymers, maleic acid derivatives, such as e.g. Gantrez® ES 225, Gantrez® ES 425, methylvinyl ether/maleic acid anhydride copolymers and their esters, non-crosslinked polyacrylic acids and polyacrylic acids crosslinked with polyols, acrylamido propyl trimethylammonium chloride/acrylate copolymers, octylacryl amidelmethyl methacrylate/tert.-butylaminoethyl methacrylate/2-hydroxyproyl methacrylate-copolymers, polycrotoneate, such as e.g. Luviset® CA 66 or Luviset® CAP (BASF), Resyn® 28-1310 or Resyn® 28-2930 (National Starch), polyvinyl pyrrolidone, vinyl pyrrolidoneldimethyl aminoethyl methacrylate/vinyl caprolactame terpolymers as well as possibly derivatised cellulose ethers and silicones. Preferably used are polyvinyl pyrrolidonelvinyl acetat copolymers (PVPNA) as well as polyvinyl pyrrolidone/vinyl acetate/vinyl pyrrolidone copolymers (PVPNANVP), such as e.g. Luviskol® VAP (BASF) or polyvinyl/caprolactame copolymers (PVCap), such as e.g. Luviskol® Plus (BASF), which for example are marketed under the name Luviskol® of BASF. A summary of suitable styling polymers can further be found in the papers of Pfrommer on the occasion of the DGK advanced training conference "Hair Treatment" ("Haarbehandlung") 1998.

Suitable cationic polymers are for example cationic cellulose derivatives, such as e.g. a quatemized hydroxyethyl cellulose, which is available under the name of Polymer JR 400® from Amerchol, cationic starch, copolymers of diallyl ammonium salts and acrylamides, quaternized vinylpyrrolidone/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequat® L /Grünau), quaternized wheat polypeptides, polyethyleneimine, cationic silicone polymers, such as e.g. amidomethicones, copolymers of adipic acid and dimethylamino hydroxypropyl diethylenetriamine (Cartaretine®/Sandoz), copolymers of acrylic acid with dimethyl diallylammonium chloride (Merquat® 550/Chemviron), polyamino polyamides, such as e.g. described in FR 2252840 A, as well as their cross-linked water soluble polymers, cationic chitin derivatives such as for example quaternized chitosane, possibly micro crystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quatemised ammonium salt polymers, such as e.g. Mirapol® A-15, Mirapol® AD-1, Mirapol® AZ-1 from Miranol.

Chitosan and Chitosan Derivatives

In a preferable embodiment of the invention the preparations in addition to glucans, for further improvement of the hair cosmetic preparations of the polymers, contain chitosans and/or chitosan derivatives. Chitosans are biopolymers and belong to the group of hydrocolloids. From a chemical point of view they are partial deacetylated chitins with different molecular weights, and contain the following - idealized - monomer module:

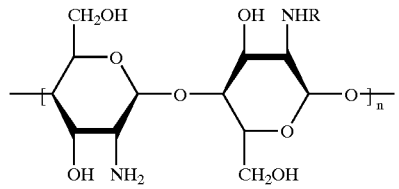

In contrast to most of the hydrocolloids, which are negatively charged in the range of biological pH-values, chitosans are under these conditions cationic biopolymers. The positively charged chitosans can interact with opposite charged surfaces and are therefore used in cosmetic hair and body care agents as well as in pharmaceutical preparations (see *Ullmann's Encyclopedia of Industrial Chemistry*, 5th Ed., vol. A6, Weinheim, Verlag Chemie, 1986, p. 231–332). A summary of these subjects are also published in for example B. Gesslein et al., HAPPI 27, 57 (1990), O. Skaugrud in *Drug Cosm. Ind.* 148. 24 (1991) and E. Onsoyen et al. in *Seifen-Öle-Fette-Wachse* 117, 633 (1991). By the production of chitosan chitin is used as starting material, preferably the shell residues of crust animals, which are available in large amounts as cheap raw materials. The chitin is thereby, using a method which first was described by Hackmann et al., usually first deprotonated by addition of bases, demineralized by addition of mineral acids and at last deacetylated by addition of strong bases, whereby the molecular weights can be distributed over a broad spectrum. Corresponding methods are for example known from *Makromol. Chem.* 177 3589 (1976) or the French patent application FR-A1 2701266. Preferably use is made of such types which are described in the German patent applications DE-A1 4442987 and DE-A1 19537001 (Henkel), and which have an average molecular weight of 50 000 to 500 000, or 800 000 to 1 200 000 Daltons, a viscosity according to Brookfield (1% by weight in glycolic acid) below 5 000 mPas, a degree of deacetylation in the range of 80 to 88% and a content of ashes of less than 0,3% by weight. In addition to the chitosanes as typical cationic biopolymers come according to the invention also in question anionic, respectively nonionic derivatized chitosans, such as e.g. carboxylation, succinilation or alkoxylation products, as they are described for example in the German patent DE-C2 3713099 (L'Oreal) as well as in the German patent application DE-A1 19604180 (Henkel).

The preparations according to the invention typically contain:
(a) 0.01 to 5, preferably 0.1 to 1 and especially 0.2 to 0.5% by weight of water soluble β-(1,3) glucans, which are substantially free from β-(1,6) linkages,
(b) 0.1 to 5, preferably 0.1 to 3 and especially 0.5 to 1% by weight of polymers, and
(c) 0 to 5, preferably 0.1 to 3 and especially 0.5 to 1% by weight of chitosans and/or chitosan derivatives,
provided that the stated amounts with water and possible further auxiliary and additional substances summarize to 100% by weight. Especially preferred preparations contain the components (a) and (b) in weight ratios 1:10 to 1:100, preferably 1:25 to 1:80 and especially 1:40 to 1:60.

Commertcial Applicability

After having improved significantly the hair cosmetic properties of polymers by adding only small amounts of the specific glucanes, a further task of the invention is the use of the mixtures, containing
(a) water soluble β-(1,3) glucans, which are substantially free from β-(1,6) linkages, and
(b) polymers
for the production of hair care agents, in which they may constitute amounts of 0.02 to 10, preferably 0.5 to 5 and especially 1 to 3% by weight, based on the agents.

The preparations according to the invention, such as for example hair shampoos, hair lotions, hair curing agents, lair finishes, hair sprays, hair colouring agents, may further as additional auxiliary and additional agents contain mild surfactants, oil bodies, emulsifiers, hyperfatting agents, pearl lustre waxes, consistency substances, thickening agents, polymers, silicone compounds, fats, waxes, stabilizing agents, biogenic active substances, deodorants, agents against dandruff, swelling agents, UV light protection agents, antioxidants, inorganic colour pigments, hydrotropes, preservatives, insect repellents, solubilizing agents, perfume oils, colouring agents and suchlike.

Typical examples of suitable mild, i.e. especially skin compatible surfactants. are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefine sulphonates, ethercarboxylic acids, alkyl oligoglucosides, fatty acid glucamides, alkylamido betaines and/or protein fatty acid condensates, the last mentioned preferably based on wheat proteins.

As oil bodies use can be made of for example Guerbet alcohols based on fatty alcohols with 6 to 18, preferably 8 to 10 carbon atoms, esters of linear $C_6$–$C_{22}$ fatty acids with linear $C_6$–$C_{22}$ fatty alcohols, esters of branched $C_6$–$C_{13}$ carboxylic acids with linear $C_6$–$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In additon esters of linear $C_6$–$C_{22}$ fatty acids with branched alcohols, especially 2-ethylhexanol, esters of hydroxycarboxylic acids with linear or branched $C_6$–$C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6$–$C_{10}$ fatty acids, liquid mixtures of mono-/di-/ triglycerides based on $C_6$–$C_{18}$ fatty acids, esters of $C_6$–$C_{22}$ fatty alcohols and/or Guerbet alcohols with aromatic carboxylic acids, especially benzoic acid, esters of $C_2$–$C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolv® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used.

As emulsifiers for example nonionic surfactants from at least one of the following groups may be used:

(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;

(2) $C_{12/18}$ fatty acid mono- and -diesters of addition products of 1 to 30 moles ethylene oxide and glycerol;

(3) glycerol mono- and diesters and sorbitan mono- and diesters of saturated and unsaturated fatty acids with 6 to 22 carbon atoms and their ethylene oxide addition products;

(4) alkyl mono- and oligoglycosides with 8 to 22 carbon atoms in the alkyl group and their ethoxylated analogues;

(5) addition products of 15 to 60 moles ethylene oxide on ricinus oil and/or hardened ricinus oil;

(6) polyol and especially polyglycerol esters, such as e.g. polyglycerol polyricinoleate, polyglycerol poly-12-hydroxystearate or polyglycerol dimerate isostearate, and also mixtures of compounds from more of these classes of substances;

(7) addition products of 2 to 15 moles ethylene oxide on ricinus oil and/or hardened ricinus oil;

(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);

(9) mono-, di- and trialkylphosphates as well as mono-, di- and/or tri-PEG alkylphosphates and their salts;

(10) wool wax alcohols;

(11) polysiloxane/polyalkyl/polyether copolymers or corresponding derivatives;

(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,

(13) polyalkylene glycols, as well as

(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on ricinus oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{2/18}$ fatty acid mono- and -diesters of addition products of ethylene oxide on glycerol are known from DE 2024051 PS as revertive fatting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologues which is usual for such products of technical quality.

Zwitterionic surfactants can also be used as emulsifiers. The term zwitterionic surfactants is intended to mean such surface active compounds which in their molecule have at least a quatenary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylaminopropyl-N,N-dimethyl ammonium glycinate, for example the coco acylaminopropyl dimethyl ammonium glycinate, and 2-alkyl-3-carboxylmethyl-hydroxyethyl imidazoline with in each case 8 to 18 C atoms in the alkyl or acyl -groups, as well as the coco acylaminoethyl hydroxyethylcarboxymethyl glycinate. Especially preferred is that under the CTFA term cocamidopropyl betaine known fatty acid amide derivative. Also suitable emulsifiers are ampholytic surfactants. Ampholytic surfactants are such surface active compounds which in addition to a $C_{8/18}$ alkyl or acyl group in the molecule at least contain a free amino group and at least one —COOH or —$SO_3H$ group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylaminopropionate and the $C_{2/18}$ acylsarcosine. In addition to the ampholytic, also quaternary emulsifiers can be used, of which ester salts of the type of esterquats, preferably methylquaternised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As exemplary pearl gloss waxes the following should be mentioned: Alkylene glycolester, especially ethyleneglycol distearate; fatty acid alkanolamides, especially coco fatty acid diethanolamide; partial glycerides, especially stearic acid monoglyceride; esters of polyvalent, possibly hydroxysubstituted carboxylic acids with fatty alcohols with 6 to 22 carbon atoms, especially long chain esters of tartaric acid; fat substances, such as for example fatty alcohols, fatty ketones, fatty aldehydes, fatty ethers and fatty carbonates, wherin the sum of carbon atoms is at least 24, especially lauron and distearyl ethers; fatty acids such as stearic acid, hydroxystearic acid or behenic acid, ring opening products of olefine epoxides with 12 to 22 carbon atoms with fatty alcohols with 12 to 22 carbon atoms and/or polyols with 2 to 15 carbon atoms and 2 to 10 hydroxyl groups as well as their mixtures.

As consistency givers preferably use is made of fatty alcohols or hydroxy fatty alcohols with 12 to 22 and preferably 16 to 18 carbon atoms and additionally partial glycerides, fatty acids or hydroxy fatty acids. A combination of these substances with alkyl oligoglucosides and/or fatty acid-N-methyl glucamides with the same chain length and/or polyglycerol-poly-12-hydroxy stearates.

Suitable thickening agents are for example types of aerosil (hydrophilic silicic acids), polysaccharides, especially xanthan gum, guar-guar, agar-agar, alginates and tyloses, carboxymethyl celluloses and hydroxyethyl celluloses, as well as higher molecular polyethylenglycol mono- and diesters of fatty acids, polyacrylates, (e.g. Carbopols® from Goodrich or Synthalenes® from Sigma), poly-acrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as elektrolytes such as sodium chloride and ammonium chloride.

Suitable silicon compounds are for example dimethyl polysiloxane, methylphenyl polysiloxane, cyclic silicones as well as amino, fatty acid, alcohol, polyether, epoxy, fluorine, glykoside and/or alkyl modified silicon compounds, which at room temperatur can be in the liquid as well as in the resin state. Further suitable are simethicones, which are mixtures of dimethicones with an average chain length of 200 to 300 dimethyl siloxane units and hydrogenated silicates. A detailed survey of suitable volatile silicones can also be found in Todd et al., *Cosm. Toil.* 91, 27 (1976).

Typical exemplary fats are glycerides, and as waxes natural waxes among others, can be used, such as e.g. candelilla wax, carnauba wax, Japan wax, espartogras wax, cork wax, guaruma wax, rice seed oil wax, sugar cane wax, ouricury wax, montan wax, beeswax, schellak wax, spermaceti, lanolin (wool wax), bürzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, aminoacids, ceramides, pseudoceramides, essential oils, extracts of plants and vitamin complexes.

As deo active agents e.g. antiperspirants such as aluminium chlorohydrate come into question. This agent is in the form of colourless, hygroscopic crystals, which easily melt in air, and is obtained through evaporation of solutions of aluminium chloride in water. Aluminium chlorohydrate is used for manufacturing of perspiration inhibiting and deodorising preparations and has probably its effect through the partial closure of the perspiratory gland by means of precipitation of proteins and/or polysaccharides [see *J.Soc. Cosm.Chem.* 24, 281 (1973)]. Under the trade name Locron® of Hoechst AG, Frankfurt/FRG, an aluminium chlorohydrate is for example on the market, which corresponds to the formula [AI$_2$(OH)$_5$CI].2.5 H$_2$O, and use of this is especially preferred (see *J.Pharm.Pharmacol.* 26 531 (1975)]. In addition to the chlorohydrates also aluminium hydroxylactates as well as acid aluminium/zirconium salts can be used. As further deo active agents esterase inhibitors can be added. These are preferably trialkyl citrates such as trimethyl citrate, tripropyl citrate, triisopropyl citrate, tributyl citrate and especially triethyl citrate (Hydagen® CAT, Henkel KGaA, Düsseldorf/FRG). The substances inhibit the enzyme activity and thereby reduce the formation of odours. Probably the free acid is thereby set free through the cleavage of the citric acid ester, and this acid lowers the pH value of the skin so much that the enzymes thereby are inhibited. Further substances which can be used as estersase inhibitors are sterol sulphates or phosphates, such as for example lanosterol, cholesterol, campesterol, stigmasterol and sitosterol sulphate or phosphate, Dicarboxylic acids and their esters, such as for example glutaric acid, glutaric acid monoethylester, glutaric acid diethylester, adipic acid, adipic acid monoethylester, adipic acid diethylester, malonic acid and malonic acid diethylester, hydroxycarboxylic acids and their esters, such as for example citric acid, malic acid, tartaric acid or tartaric acid diethylester. Antibacterial active substances, which influence the germ flora and kill sweat destroyng bacterias or inhibit their growth, can also be contained in the pin preparations. Examples of this are chitosan, phenoxyethanol and chlorohexidin gluconate. Also 5-chloro-2-(2,4-dichlorophen-oxy)-phenol has shown to have an especially good effect, and this product is marketed unter the trade name Irgasan® by Ciba-Geigy, Basel/CH.

As anti dandruff agents climbazol, octopirox and zinc pyrethion can be used. As swelling agents for aqueous phases montmorillonite, clay mineral substances, pemulen, as well as alkylmodified Carbopol types (Goodrich) can be used. Further suitable polymers or swelling agents can be found in the survey of R.Lochhead in Cosm. Toil. 108, 95 (1993).

UV light protection factors are e.g organic substances (light protection filters) which by room temperature are in liquid or crystalline form, and which are capable of absorbing ultraviolet radiation and to set free the received energy in the form of radiation with long wavelength, e.g. in the form of heat. UVB filters can be soluble in oils or in water. As oil soluble substances the following are mentioned as examples:

3-Benzyliden camphor, respectively 3-benzylidene norcamphor and the derivatives thereof, e.g. 3-(4-methylbenzylidene) camphor as described in EP-B1 0693471;

4-aminobenzoic acid derivatives, preferably 4-(dimethylamino) benzoic acid 2-ethylhexylester, 4-(dimethylamino) benzoic acid 2-octylester and 4-(dimethylamino) benzoic acid amylester;

esters of cinnamonic acid, preferably 4-methoxy cinnamonic acid 2-ethylhexylester, 4-methoxy cinnamonic acid propylester, 4-methoxy cinnamonic acid isoamylester, 2-cyano-3,3-phenyl cinnamonic acid 2-ethythexylester (octocrylene);

esters of salicylic acid, preferably salicylic acid 2-ethylhexylester, salicylic acid 4-isopropyl benzylester, salicylic acid homomenthylester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino-(p-carbo-2'-ethyl-1'-hexyloxy)-1,3,5-triazine and octyltriazone, as described in EP A1 0818450;

propane-1,3-diones, such as e.g. 1-(4-tert.-butylphenyl)-3-(4'-methoxy-phenyl)-propane-1,3-dion;

ketotricyclo(5,2,1,0)-decane derivatives, as described in EP-B1 06945521. As water soluble substances the following can be mentioned:

2-Phenylbenzimidazol-5-sulphonic acid and the alkali, alkaline earth, ammonium, alkylammonium, alkanolammonium and glucammonium salts;

sulphonic acid derivatives of benzophenones, preferably 2-hydroxy-4-methoxybenzophenon-5-sulphonic acid and their salts;

sulphonic acid derivatives of 3-benzylidencamphen, such as e.g. 4-(2-oxo-3-bomylidenmethyl)-benzene sulphonic acid and 2-methyl-5-(2-oxo-bomyliden) sulphonic acid and their salts.

As typical UV-A filters especially derivatives of benzoyl methane comes in question, such as e.g. 1-(4'-tert.-butylphenyl)-3-(4'-methoxyphenyl)propane-1,3-dion, 4-tert.butyl-4'-methoxydibenzoyl-methane (Parsol 1789), or 1-phenyl-3-(4'-isopropylphenyl-propane-1,3-dion. The UV-A and UV-B filters can of course also be used in mixtures. In this case combinations of octocrylene or camphor derivatives with butyl methoxydibenzoyl methane are especially photosensitive.

In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (talk), barium sulphate or zinc stearate can be used. The oxides and salts are used in the form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. In sun protecting agents preferably so-called micro or nano pigments are used. Preferably micronized zinc oxide is used. Further suitable UV light protection factors can be found in the survey by P.Finkel in SÖFW-Joumal 122, 543 (1996). Likewise suitable are herbal extracts with UV absorbing or antioxidative properties.

In addition to the primary light protection substances also secondary light protection substances of the antioxidant type find use, which interrupt the photochemichal reaction chain, which is initiated when UV radiation penetrates the skin. Typical examples of such are amino acids (e.g. glycin, histidin, tyrosin, tryptophan) and their derivatives, imidazoles (e.g. urocaninic acid) and their derivatives, peptides such as D,L-camosine, D-camosine, L-camosine and their derivatives (e.g. anserine), carotinoides, carotine (e.g. α-carotin, α-carotin, lycopin) and their derivatives, chlorogenic acid and its derivatives, liponic acid and its derivatives (e.g. dihydroliponic acid), aurothioglucose, propylthiouracil and other thiols (e.g. thioredoxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to $\mu$mol/kg), further (metal) chelating agents (e.g. α-hydroxy fatty acids, palmitic acid, phytinic acid, lactoferrine), α-hydroxy acids (e.g. citric acid, lactic acid, malic acid), humin acid, gallic acid, gallic extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopheroles and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, camosine, butylhydroxy toluene, butylhydroxy anisol, nordihydro guajak resin acid, nordihydro guajaret acid, trihydroxy butyrophenon, uric acid and their derivatives, mannose and its derivatives, super oxide dismutase, zinc and its derivatives (e.g. ZnO, ZnSO$_4$), selen and its derivatives (e.g. selen-methionin), stilbenes and their derivatives (e.g. stilben oxide, trans-stilben oxide) and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. The polyols can further contain additional functional groups, especially amino groups, or be modified with nitrogen. Typical examples are:

Glycerol;

alkylen glycols, such as for example ethylene glycol, diethylene glycol, propylene glycol, butylene glycol, hexylene glycol as well as polyethylen glycols with an average molecular weight from 100 to 1 000 Daltons;

oligoglycerol mixtures of technical quality with a self-condensation degree of 1.5 to 10, such as e.g. technical quality diglycerol mixtures with a diglycerol content of 40 to 50% by weight;

methyol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

aminosugars, such as for example glucamine;

dialcoholamines, such as diethanolamine or 2-amino-1, 3-propanediol.

As preservatives for example phenoxyethanol, formaldehyde solution, parabene, pentanediol or sorbic acid as well as those mentioned in enclosure 6, parts A and B of the cosmetic regulation, are further classes of substances. As insect repellents N,N-diethyl-m-toluamide, 1,2-pentanediol or insect repellent 3535 come into question, as self tanning agent dihydroxyaceton is suited.

As perfume oils mixtures of natural and synthetic scent substances should be mentioned. Natural scent substances are extracts of flowers (lilies, lavender, roses, jasmin, neroli, ylang-ylang), stems and blades (geranium, patchouli, petitgrain), fruits (anis, coriander, caraway, juniper), fruit shells (bergamot, lemon, range), roots (macis, angelica, celery, kardamon, costus, iris, calmus), wood stone pine, sandel, guajac, cedar, rosewood), herbs and grass (tarragon, emongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzyl-carbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, -isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiver oil, oliban oil, galbanum oil, labolanum oil and lavandin oil. Preferably used are bergamot oil, dihydromyrcenol, lilial, lyral, citronellol, phenylethyl alcohol, α-hexylcinnamon aldehyde, geraniol, benzylaceton, cyclamen aldehyde, linalool, boisambrene forte, ambroxane, indol, hedione, sandelice, lemon oil, mandarin oil, orangenoil, allylamyl glycolate, cyclovertal, lavandine oil, muskateller sage oil, β-damascone, geranium oil bourbon, cyclohexyl salicylate, vertofix coeur, iso-E-super, fixolide NP, evemyl, iraidein gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication "Kosmetische Färbemittel", (cosmetic dyes) of the "Farbstoffkommission der Deutschen Forschungsgemeinschaft", published by Verlag Chemie, Weinheim, 1984, p. 81–106. These dyes are generally used in concentrations from 0.001 to 0.1% by weight, based on the whole mixture.

Typical examples of germ inhibiting substances are preservatives with specific effects against gram-positive bacteria, such as 2,4,4'-trichloro-2'-hydroxy diphenylether, chlorohexidin (1,6-di-(4-chlorophenyl-biguanido-hexan) or TCC (3,4,4'-trichlorocarbanilide). Many scent substances and etheral oils also have antimicrobial properties. Typical examples are the active agents eugenol, menthol and thymol in carnation, mint and thyme oil. An interesting natural deo substance is the terpene alcohol farnesol (3,7,1 1-trimethyl-2,6,10-dodecatrien-1-ol), which is present in lime flower oil and has a smell of lilies of the valley. Also glycerol monolaurate have been used as bacteriostaticum. Normally the content of the further germ inhibiting agent is about 0.1 to 2% by weight - based on the solids content of the preparations.

The cumulative contents of the auxiliary and additional agents can be 1 to 50, preferably 5 to 40% by weight, based on the agents. The manufacture of the agents can take place by common cold or hot processes; preferably the work is carried out according to the phase inversion temperature method.

EXAMPLES

For the determination of the film hardness the measuring system according to Konig for determination of the pendulum hardness was used (seconds pendulum hardness by 6° deflection; apparatus Erichsen 299/300, Hermer/Sundvig), which as result gives the hardness of a laquer film. For this purpose different test solutions were placed on an object slide and air dried. The procedure was repeated many times, until a dried film with a thickness of 30 μm had been obtained. The measurement took place by placing a pendulum on the film, which was braught to vibration by a constant starting deflection. For the determination of the results of the measurements the number of penulum deflections until the minimum deflection was counted and multiplied with the duration of the vibration (1,4). For examination of the stress crack formation, films with a layer thickness of approximately 30 μm after drying were examined microscopically. In this case (−) means strong stress cracks, (o) fine stress cracks and (+) no stress carcks. The results are summarized in Tale 1. The examples 1 to 6 are according to the invention, the examples V1 and V2 are for comparison.

TABLE 1

| | Film hardness and stress crack formation | | | | | | | |
|---|---|---|---|---|---|---|---|---|
| Composition/Performance | 1 | 2 | 3 | 4 | 5 | 7 | V1 | V2 |
| Betaglucan[1] | 0.1 | 0.2 | 0.3 | 0.4 | 0.5 | 0.4 | — | — |
| Polyvinyl pyrrolidone/vinyl acetate copolymer[2] | 4.0 | 4.0 | 4.0 | 4.0 | 4.0 | 4.0 | 4.0 | 4.0 |
| Chitosan[3] | | | | | | 0.1 | — | 0.1 |
| Water | | | | ad 100 | | | | |
| Pendelum hardness | 149 | 152 | 153 | 155 | 159 | 159 | 148 | 149 |
| Apperance of the dried film | + | + | + | + | + | + | − | o |

[1]Highcareen ® GS/Henkel;
[2]Luviskol ® VA 64/BASF;
[3]Hydragen HCMF/Henkel

We claim:
1. Hair cosmetic preparations, containing
   (a) water soluble β-(1,3) glucans, substantially free from β-(1,6) linkages, and
   (b) polymers.
2. Preparations according to claim 1, which contain glucans which are obtained based on yeasts from the family Saccharomyces.
3. Preparations according to claim 1, which contain glucans which are obtained by contacting glucans with β-(1,3) and β-(1,6) linkages with β-(1,6) glucanases, in such a way that practically all β-(1,6) linkages are loosened.
4. Preparations according to claim 1, which contain film forming polymers.

5. Preparations according to claim 1, which contain anionic, nonionic, amphoteric and/or zwitterionic polymers.

6. Preparations according to claim 5, which contain polyvinyl pyrroldone/vinyl acetate copolymers.

7. Preparations according to claim 1, which contain cationic polymers.

8. Preparations according to claim 1, which contain chitosans, respectively chitosan derivatives.

9. Preparations according to claim 1, which contain
   (a) 0.01 to 5% by weight of water soluble $\beta$-(1,3) glucans, which are substantially free from $\beta$-(1,6)-linkages,
   (b) 0.1 to 5% by weight of polymers, and
   (c) 0 to 5% by weight of chitosans and/or chitosan derivatives, provided that the stated amounts with water and possible further auxiliary and additional substances summarize to 100% by weight.

10. Method of preparing hair care products comprising
   a. water soluble $\beta$-(1,3) glucans, substantially free from $\beta$-(1,6) linkages, and
   b. polymers.

* * * * *